United States Patent [19]

Mar

[11] Patent Number: 4,644,807

[45] Date of Patent: Feb. 24, 1987

[54] FLUID SAMPLE DELIVERY APPARATUS

[75] Inventor: Dav Mar, Sunnyvale, Calif.

[73] Assignee: Dionex Corporation, Sunnyvale, Calif.

[21] Appl. No.: 703,861

[22] Filed: Feb. 21, 1985

[51] Int. Cl.⁴ ............................................. G01N 1/14
[52] U.S. Cl. ................................... 73/864.62; 141/27; 222/387; 422/100; 73/864.87; 73/863.23; 73/864.91
[58] Field of Search ........... 73/864.87, 864.62, 864.81, 73/864.85, 863.23, 864.91, 863.25, 864.86, 864.34, 864.35, 61.1 C, 863.24; 422/101, 102, 103, 70, 100; 222/387, 386; 141/27

[56] References Cited

U.S. PATENT DOCUMENTS

| | | | |
|---|---|---|---|
| 714,212 | 11/1902 | Marks | 222/386 X |
| 764,564 | 7/1904 | Dreyer | 422/100 X |
| 1,217,663 | 2/1917 | Taylor | 141/27 |
| 3,481,477 | 12/1969 | Farr | 210/359 |
| 3,512,940 | 5/1970 | Shapiro | 422/101 |
| 3,586,064 | 6/1971 | Brown et al. | 141/327 X |
| 3,590,889 | 7/1971 | Vannus | 141/329 X |
| 3,693,804 | 9/1972 | Grover | 210/359 |
| 3,735,900 | 5/1973 | Gores | 222/386 X |
| 3,832,141 | 8/1974 | Haldopoulos | 422/101 |
| 3,837,376 | 9/1974 | Brown et al. | 141/327 X |
| 3,846,077 | 11/1974 | Ohringer | 73/863.23 X |
| 3,918,913 | 11/1975 | Stevens et al. | 73/864.24 X |
| 3,955,423 | 5/1976 | Ohringer | 73/864.91 X |
| 4,037,464 | 7/1977 | Wenander | 422/100 X |
| 4,057,499 | 11/1977 | Buono | 422/101 X |
| 4,197,735 | 4/1980 | Munzer et al. | 422/103 X |
| 4,318,803 | 3/1982 | Holmgren | 422/101 X |
| 4,403,518 | 9/1983 | Welker | 73/864.34 |
| 4,409,850 | 10/1983 | Zeck | 73/864.62 |
| 4,440,032 | 4/1984 | Welker | 73/864.34 X |
| 4,483,825 | 11/1984 | Fatches | 422/100 |

FOREIGN PATENT DOCUMENTS 804095 11/1958 United Kingdom ............... 222/386

*Primary Examiner*—Stewart J. Levy
*Assistant Examiner*—Tom Noland
*Attorney, Agent, or Firm*—Flehr, Hohbach, Test, Albritton & Herbert

[57] ABSTRACT

Apparatus for delivering samples of liquid to be analyzed in a chromatographic column. The sample is placed in a vial having a compressible plunger slideably mounted therein. The sample is delivered by depressing the plunger with a sampling tip, and the sample is delivered to the tip through a passageway in the plunger. The tip interfits with the plunger to form a fluid-tight seal yet is readily disengaged therefrom. The plunger and the bottom wall of the vial have matching contours which eliminate air from the sample and assure that all of the sample is delivered. A filter mounted in the plunger passageway removes particulate matter from the sample delivered to the tip.

17 Claims, 3 Drawing Figures

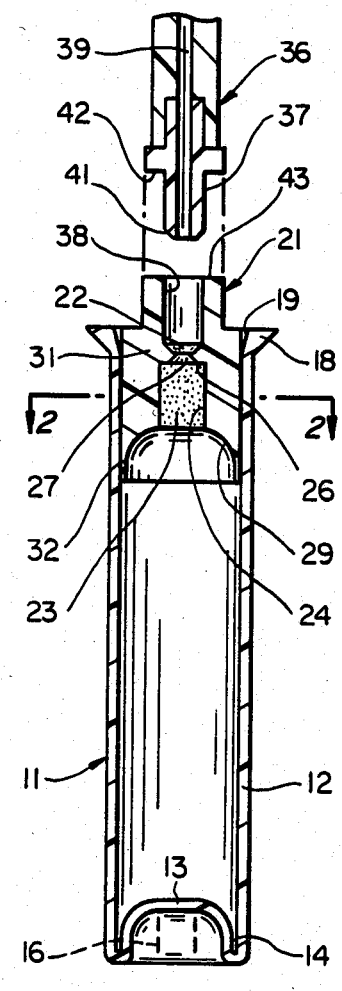
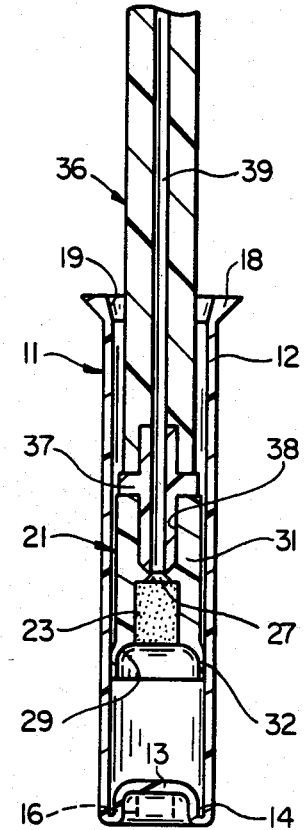
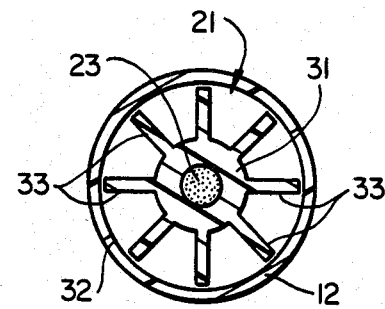
FIG_1  FIG_3
FIG_2

FLUID SAMPLE DELIVERY APPARATUS

BACKGROUND OF THE INVENTION

1. Field of the Invention

This invention pertains generally to liquid chromatography, and more particularly to apparatus for delivering samples of liquid to be analyzed in a chromatographic column.

2. Description of the Related Art

A number of different techniques have heretofore been employed for delivering liquid samples to chromatographic columns. In one such technique, the sample is placed in a syringe which is attached to a hollow metal needle. The sample is delivered to the column manually by piercing a septum with the metal needle and injecting the sample into the column.

U.S. Pat. No. 3,918,913 describes a system in which a stopper in a cylindrical container is pierced by a hollow metal needle which drives the stopper into the container in piston-like fashion, forcing the liquid sample out of the container through the opening in the needle.

These prior art systems have certain limitations and disadvantages. They all require a metal needle which pierces a seal in one form or another, and they may also require a separate metering stage to accurately control the amount of liquid delivered to the column. Even with metals of high quality, such as high alloy stainless steel, metal ions from the needle can be detected in the sample by the chromatographic instrument.

It is in general an object of the invention to provide new and improved apparatus for delivering a sample to a chromatographic column.

Another object of the invention is to provide apparatus of the above character which overcomes the foregoing and other limitations and disadvantages of the sample delivery systems heretofore provided.

SUMMARY OF THE INVENTION

These and other objects are achieved in accordance with the invention by providing a sample holding vial having a side wall and a bottom wall, with a plunger slideably mounted in the vial in sealing engagement with the side wall. The plunger has an axially extending passageway through which the sample is discharged as the plunger is depressed in the vial. A sampling tip movable between axially extended and retracted positions engages the plunger to depress the same in the vial. The sampling tip and the plunger have mating plug and socket portions which form a fluid-tight seal through which the sample is delivered to the tip. The bottom wall of the vial is upwardly convex, and the lower side of the plunger is upwardly concave and mates closely with the bottom wall whereby substantially all of the sample is delivered from the vial when the plunger is depressed to the bottom of the vial. The plunger fits tightly in the bottom portion of the vial, and the force required to seat and separate the plug and socket portions of the sampling tip and the plunger is less than the force required to depress the plunger initially or to dislodge it from the bottom of the vial. This assures that the tip is in sealing engagement with the plunger before the plunger starts to move and permits the plunger to remain at the bottom of the vial when the tip is retracted.

BRIEF DESCRIPTION OF THE DRAWINGS

FIG. 1 is a centerline sectional view of one embodiment of sample delivery apparatus according to the invention.

FIG. 2 is a cross-sectional view taken along line 2—2 in FIG. 1.

FIG. 3 is a centerline sectional view of a second embodiment of sample delivery apparatus according to the invention.

DETAILED DESCRIPTION

As illustrated in FIG. 1, the sample delivery apparatus includes a sample holding vial 11 which has a cylindrical side wall 12 and an upwardly convex or domed bottom wall 13. A relatively narrow annular space 14 is formed at the junction of the side wall and the bottom wall, and shallow grooves 16 are formed in the upper surface of the bottom wall to prevent fluid from becoming trapped in the annular space. A conically tapered flange 18 extends outwardly from the upper end of side wall 12 and is received in a mating socket of a vial holder or cassette (not shown) whereby the vial can be supported in an upright position in the cassette. The upper portion of the inner side wall is flared or chamfered, as indicated at 19, to facilitate insertion of a plunger into the vial.

A plunger 21 is slideably mounted in the vial in sealing engagement with side wall 12. This plunger has an axially extending passageway 22 through which fluid is delivered when the plunger is depressed or moved toward the bottom of the vial. A microporous filter 23 is mounted in a counterbore 24 at the lower end of the passageway. This filter removes particulate matter from the sample delivered through the passageway and is substantially impervious to vapors when the plunger is at rest. The filter seats against an annular shoulder 26 at the upper end of the counterbore, and the passageway immediately above the filter is conically tapered, as indicated at 27, to prevent bubbles from being trapped above the filter. The junction between the side wall and the upper wall of the counterbore is radiused or curved to further prevent the trapping of bubbles.

The lower side of the plunger is upwardly concave, as indicated at 29, and it mates closely with the upwardly convex bottom wall 13 when the plunger is fully depressed in the vial. While other matching contours can be employed for the purpose of eliminating dead volume, the domed or spherically curved contour illustrated is preferred because it allows any air trapped above the fluid in the vial to be collected and voided with the initial depression or downward movement of the plunger. With the air removed in this manner, no bubbling occurs once the flow of fluid begins. The spherical contour on the bottom wall has the additional advantage of providing maximum strength to withstand internal pressure with minimal thickness.

In the embodiment of FIG. 1, plunger 21 has a core 31 with a depending skirt 32 at the lower end of the core. Fins 33 extend radially from the core and engage side wall 12 to prevent cocking of the plunger in the vial. This finned structure minimizes the area of contact and, hence friction between the plunger and the side wall, and it reduces thickness of sections to aid in molding. The diameter of the fins is slightly less than the internal diameter of the side wall. Skirt 32 has a slightly greater diameter than the side wall, and it forms a fluid-tight seal with the side wall. The skirt is relatively thin, and it is urged outwardly against the side wall of the vial by pressurization of the fluid sample as the plunger is depressed or moved toward the bottom of the vial.

The skirt of the plunger is received in annular space 14 when the plunger is fully depressed in the vial. The thickness of the skirt is slightly greater than the width of the annular space so that the plunger fits tightly and is held at the bottom of the vial.

The plunger is depressed in the vial by means of a sampling tip 36 which is engageable with the upper portion of the plunger and movable between axially extended and retracted positions. The sampling tip has a plug 37 which mates with a socket 38 in the upper portion of the plunger to form a fluid-tight seal. The tip has an axially extending passageway 39 which communicates with the passageway in the plunger when the plug is seated in the socket. The side walls of the plug and the socket each have a Luer taper to provide a radial seal between the two parts. The lower end of the plug is chamfered, as indicated at 41, to facilitate insertion of the plug into the socket, and a matching contour is provided at the bottom of the socket. The plug has a radial shoulder 42 which engages the upper surface 43 of the plunger. The dimensions of the plug and socket are such that some interference exists between the male and female Luer tapers before the driving shoulder engages the top part of the plunger and before the tip of the plug is fully seated in the bottom of the socket. Once the plug is fully seated, a butt seal is provided between the tip and the bottom of the socket in addition to the radial seal provided by the Luer tapers.

Vial 11 and plunger 21 can be fabricated by molding or another suitable process. In one presently preferred embodiment, the vial is fabricated of a relatively inert thermoplastic material which is compatible with strong acids, bases and solvents, yet is strong enough to withstand the internal pressure developed when the plunger is depressed. The plunger is preferably fabricated of a thermoplastic material which is compatible with strong acids, bases and solvents and is sufficiently pliable in thin sections such as skirt 32 to conform to the internal wall of the vial as the plunger is depressed. The small quantities of materials necessary to form such parts are relatively inexpensive, and the parts can be discarded after use. The shape of the mating tip and plunger allows the tip to be fabricated of a more inert material of less strength, and there are no metal ions to contaminate the samples.

The dimensions of the parts are preferably such that the force required to initiate downward movement of the plunger is greater than the force required to seat the sampling tip in the plunger, and the force required to dislodge the plunger from the bottom of the vial is greater than the force required to separate the sampling tip from the plunger. This relationship assures that the sampling tip and the plunger are sealed together before the delivery of the sample begins, and it provides automatic separation of the sampling tip and the plunger once the sample has been delivered and the tip is retracted.

The vial and plunger are particularly suitable for use in an automated system in which a plurality of samples are to be delivered to a chromatographic column. The vials can be mounted in cassettes which are delivered to a sampling station where the sampling tip is located. The conical taper on flange 18 assures accurate positioning of the vials in the cassettes, and the chamfer on the lower end of the sampling tip accommodates any slight misalignment of the vials with the tip.

In operation and use, the sample is placed in the vial, and the plunger is inserted to close the vial. The plunger skirt provides a seal between the plunger and the side wall of the vial, and the microporous filter prevents evaporation of the sample through passageway 22.

The sample is discharged from the vial by a downward stroke of the sampling tip. As the tip enters socket 38, the plunger does not begin to move until the tip is fully seated in the socket. When the plunger does begin to move, any air trapped in the vial above the sample is discharged first. Once the delivery of the sample begins, it continues until the lower side of the plunger mates with the bottom wall of the vial and the plunger skirt is seated in the annular space at the bottom of the vial. Because of the close fit between the lower portions of the plunger and the vial, substantially all of the sample is discharged from the vial, and it is not necessary to employ a separate metering stage to control the amount of the sample since fluid discharged is directly proportional to downward movement of the plunger.

When the sampling tip is retracted, the plunger is held in the bottom portion of the vial due to the tight fit of the skirt in the annular space, and the tip separates from the plunger, leaving the plunger at the bottom of the vial.

The embodiment of FIG. 3 is generally similar to the embodiment of FIG. 1, and like reference numerals designate corresponding elements in the two embodiments. The second embodiment is intended primarily for smaller samples than the first embodiment, and it can be dimensioned accordingly. For example, the first embodiment might have a nominal fluid capacity of 5 ml, and the second embodiment might have a nominal capacity of 0.5 ml. To provide these capacities, the vial of the second embodiment can have a smaller diameter and length than the vial of the first embodiment.

In the second embodiment, the core 31 of plunger 21 has a diameter slightly less than the internal diameter of the vial, and no radial fins are employed in this embodiment. The cores can have the same diameter in the two embodiments to facilitate handling of the apparatus. For example, for the purpose of imparting a bit of binary information to an automated system the plungers can be positioned so that the upper portions of the plungers are either flush with or project from the tops of the vials when the vials are full, and with cores of the same diameter a single guide of fixed width can be employed in guiding plungers of either embodiment in the latter position. The plunger cores can also have the same length in the two embodiments to facilitate insertion of identical filter elements in an automated assembly operation.

Operation and use of the embodiment of FIG. 3 is identical to that described above.

It is apparent from the foregoing that a new and improved apparatus for delivering liquid samples for analysis in a chromatographic column has been provided. While only certain presently preferred embodiments have been described in detail, as will be apparent to those familiar with the art, certain changes and modifications can be made without departing from the scope of the invention as defined by the following claims.

I claim:

1. In apparatus for delivering a fluid sample: a sample holding vial having a side wall and an upwardly convex bottom wall, and a plunger slideably mounted in the vial in sealing engagement with the side wall and having an upwardly concave lower side which mates with the bottom wall of the vial when the plunger is in a depressed position at the bottom of the vial, said plunger also having an axially extending passageway through which the sample is delivered as the plunger is moved toward the depressed position.

2. The apparatus of claim 1 wherein the bottom wall of the vial and the lower side of the plunger are spherically curved.

3. The apparatus of claim 1 including a filter carried by the plunger for removing particulate matter from the sample delivered through the passageway.

4. The apparatus of claim 1 wherein the vial includes a relatively narrow annular space at the junction of the bottom wall and the side wall, and the plunger has a depending skirt which is received in the annular space when the plunger is in the depressed position.

5. The apparatus of claim 1 wherein the plunger includes an upwardly facing socket in communication with the passageway for receiving an axially movable sampling tip in sealing engagement, the plunger being moved to the depressed position by movement of the sampling tip.

6. In apparatus for delivering a fluid sample: a sample holding vial having a side wall and a bottom wall, a plunger slideably mounted in the vial in sealing engagement with the side wall and having an axially extending passageway through which the sample is delivered as the plunger is depressed in the vial, and a sampling tip engageable with the plunger and movable between axially extended and retracted positions for depressing the plunger in the vial, said sampling tip and said plunger having mating plug and socket portions forming a fluid-tight seal through which the sample is delivered to the tip, the sampling tip being seated in the socket by movement of the sampling tip, and the force required to initiate movement of the plunger being greater than the force required to seat the tip whereby the plunger does not begin to move until the tip is fully seated in the socket, the plunger including a deformable skirt which is urged outwardly against the side wall of the vial by pressurization of the fluid sample as the plunger is moved toward the bottom of the vial.

7. The apparatus of claim 6 wherein the sampling tip is fabricated of a non-metallic material.

8. The apparatus of claim 6 wherein the plunger has an upwardly facing socket which communicates with the axially extending passageway, and the sampling tip includes an end portion which is received in the socket to form the fluid-tight seal.

9. The apparatus of claim 6 including a microporous filter carried by the plunger for removing particulate matter from the sample discharged through the passageway.

10. The apparatus of claim 9 wherein the filter is mounted in a bore at the lower end of the passageway.

11. In apparatus for delivering a fluid sample: a vial having a side wall and a bottom wall, a plunger slideably mounted in the vial in sealing engagement with the side wall and displaceable in response to a predetermined force, said plunger having an axially extending passageway through which the sample is delivered as the plunger is moved toward the bottom of the vial, and a sampling tip engageable with the plunger and movable between axially extended and retracted positions for moving the plunger toward the bottom of the vial, said sampling tip and said plunger having mating plug and socket portions which form a fluid-tight seal when seated together, the force required to seat the plug and socket portions being less than the predetermined force whereby the plug is fully seated in the socket before the plunger begins to move when the sampling tip is moved toward its extended position, the plunger fitting tightly in the bottom portion of the vial and remaining at the bottom of the vial when the sampling tip is retracted with sufficient force to separate the plug and socket portions of the tip and plunger.

12. In apparatus for delivering a fluid sample: a sample holding vial having a side wall and an upwardly convex bottom wall, a plunger slideably mounted in the vial in sealing engagement with the side wall and having an axially extending passageway through which the sample is delivered as the plunger is depressed in the vial, the lower side of the plunger being upwardly concave and mating closely with the bottom wall of the vial whereby substantially all of the sample is delivered from the vial when the plunger is depressed to the bottom of the vial, and a sampling tip fabricated of a nonmetallic material engageable with the plunger and movable between axially extended and retracted positions for depressing the plunger in the vial, said sampling tip and said plunger having mating plug and socket portions forming a fluid-tight seal through which the sample is delivered to the tip.

13. The apparatus of claim 12 wherein the vial includes a relatively narrow annular space between the side wall and the bottom wall, and the plunger has a depending skirt which is received in the annular space when the plunger is depressed to the bottom of the vial.

14. The apparatus of claim 13 wherein the skirt fits tightly in the annular space and is thereby held at the bottom of the vial, the skirt being separable from the annular space by a force greater than the force required to separate the tip end from the socket whereby the plunger remains at the bottom of the vial when the tip is withdrawn from the vial.

15. In apparatus for delivering a fluid sample: a vial having a side wall and an upwardly convex bottom wall, a plunger slideably mounted in the vial insealing engagement with the side wall and displaceable in response to a predetermined force, said plunger having an axially extending passageway through which the sample is delivered as the plunger is moved toward the bottom of the vial and an upwardly concave lower side which mates closely with the bottom wall whereby substantially all of the sample is discharge from the vial when the plunger is depressed to the bottom of the vial, and a sampling tip engageable with the plunger and movable between axially extended and retracted positions for moving the plunger toward the bottom of the vial, said sampling tip and said plunger having mating plug and socket portions which form a fluid-tight seal when seated together, the force required to seat the plug and socket portions being less than the predetermined force whereby the plug is fully seated in the socket before the plunger begins to move when the sampling tip is moved toward its extended position.

16. In apparatus for delivering a fluid sample: a sample holding vial having a side wall and a bottom wall, a plunger slideably mounted in the vial in sealing engagement with the side wall and having an axially passageway through which the sample is delivered as the plunger is depressed in the vial, and a sampling tip engageable with the plunger and movable between axially extended and retracted positions for depressing the plunger in the vial, said sampling tip and said plunger having mating plug and socket portions forming a fluid-tight seal through which the sample is delivered to the tip, the sampling tip being seated in the socket by movement of the sampling tip, and the force required to initiate movement of the plunger being greater than the force required to seat the tip whereby the plunger does not begin to move until the tip is fully seated in the socket, the plunger fitting tightly in the bottom portion of the vial and remaining at the bottom of the vial when the sampling tip is retracted with sufficient force to separate the plug and socket portions of the tip and plunger.

17. In apparatus for delivering a fluid sample: a vial having a side wall and a bottom wall, a plunger slideably mounted in the vial in sealing engagement with the side wall and displaceable in response to a predetermined force, said plunger having an aially extending passageway through which the sample is delivered as the plunger is moved toward the bottom of the vial, and a sampling tip engageable: with the plunger and movable between axially extended and retracted positions for moving the plunger toward the bottom of the vial, said sampling tip and said plunger having mating plug and socket portions which form a fluid-tight seal when seated togehter, the force required to seat the plug and socket portions being less than the predetermined force whereby the plug is fully seated in the socket before the plunger begins to move when the sampling tip is moved toward its extended position, the plunger including a deformable skirt which is urged outwardly against the side wall of the vial by pressurization of the fluid sample as the plunger is moved toward the bottom of the vial.

* * * * *